(12) United States Patent
Kounaves

(10) Patent No.: US 7,632,393 B2
(45) Date of Patent: Dec. 15, 2009

(54) TOTAL ORGANIC CARBON (TOC) ANALYZER

(75) Inventor: Samuel P. Kounaves, Winchester, MA (US)

(73) Assignee: Trustees of Tufts College, Medford, MA (US)

( * ) Notice: Subject to any disclaimer, the term of this patent is extended or adjusted under 35 U.S.C. 154(b) by 834 days.

(21) Appl. No.: 10/517,584

(22) PCT Filed: Jun. 10, 2003

(86) PCT No.: PCT/US03/18164

§ 371 (c)(1), (2), (4) Date: Apr. 25, 2005

(87) PCT Pub. No.: WO03/104765

PCT Pub. Date: Dec. 18, 2003

(65) Prior Publication Data

US 2005/0226774 A1 Oct. 13, 2005

Related U.S. Application Data

(60) Provisional application No. 60/387,325, filed on Jun. 10, 2002.

(51) Int. Cl.
*G01N 27/403* (2006.01)
(52) U.S. Cl. .................. 205/785.5; 204/424
(58) Field of Classification Search ......... 205/782–783, 205/785.5, 362, 555; 204/424
See application file for complete search history.

(56) References Cited

U.S. PATENT DOCUMENTS 4,755,473 A * 7/1988 Nishino et al. ............... 436/133
5,855,760 A * 1/1999 Zen et al. ..................... 205/555
6,106,692 A * 8/2000 Kunimatsu et al. .......... 205/775
6,267,866 B1 * 7/2001 Glesener et al. ............. 205/450
2003/0170906 A1 * 9/2003 Swain et al. ................. 436/171

OTHER PUBLICATIONS

Qian et al. "Automated High-Performance, High-temperature Combustion Total Organic Carbon Analyzer," Anal. Chem. 1996, 68, 3090-3097.*

Hagans P L; Natishan P M; Stoner B R; O'Grady W E: "Electrochemical oxidation of phenol using borondoped diamond electrodes", Journal of the Electrochemical Society, vol. 148, No. 7, Jul. 2001, pp. E298-E301, XP7909722, ISSN: 0013-4651.

Hattori S; Doi M; Takahashi E; Kurosu T; Nara M; Nakamatsu S; Nishiki Y; Furuta T; Iida M: "Electrolytic decomposition of amaranth dyestuff using diamond electrodes", Journal of Applied Electrochemistry, vol. 33, No. 1, Jan. 2003, pp. 85-91, XP2377272, ISSN: 0021-891X.

* cited by examiner

*Primary Examiner*—Alex Noguerola
(74) *Attorney, Agent, or Firm*—Pierce Atwood LLP; Kevin M. Farrell; David J. Wilson

(57) ABSTRACT

The invention disclosed is a total organic carbon (TOC) analyzer comprised of an electrochemical cell comprising a diamond-film electrode (2) doped with boron or other conductivity including material. The diamond-film electrode is the working electrode and carries out the oxidation of TOC to produce carbon dioxide. The apparatus further comprises sensors for detecting the carbon dioxide produced. Such sensors include but are not limited to a tunable diode laser (1) and/or ion-selective electrode (5). The invention also discloses a method for measuring TOC in an aqueous solution using a total organic carbon analyzer.

13 Claims, 1 Drawing Sheet

US 7,632,393 B2

TOTAL ORGANIC CARBON (TOC) ANALYZER

This application is a 371 of PCT/US03/18164, filed on Jun. 10, 2003, which claims benefit from provisional application 60/387,325, filed Jun. 10, 2002.

GOVERNMENT SUPPORT

This invention was made with government support under NAG5-11806 awarded by the National Aeronautics and Space Administration. The government has certain rights in the invention.

BACKGROUND OF THE INVENTION

The measurement of total organic carbon (TOC) is frequently performed in environmental, clinical, and industrial settings. Current techniques require hazardous reagents, such as strong acid and oxidizing agents, ultraviolet light, or high temperature ovens, to carry out the oxidation reactions. The development of a safe and cost-effective electrochemical device capable of oxidizing organic carbon and determining TOC in aqueous solution would represent a significant advance in the art.

The concept of electrochemically oxidizing organics was demonstrated in the early 1990's as a technology for incineration of toxic organic industrial wastes. Unfortunately, this technology has thus far proven inefficient and of limited use. Over the years, a variety of working electrodes for electrochemically oxidizing organic carbon have been developed. The properties of a working electrode in an electrochemical cell is critically important since the working electrode is directly involved in the oxidation of the organic molecule. The most common working electrode material has typically been carbon-based or made from metals such as platinum, silver, gold, mercury, or nickel. Such electrodes, however, poorly oxidize because of their limited anodic range. These electrodes eventually themselves become oxidized, and therefore are inefficient for any practical use. To overcome these limitations, recent attention has focused on the potential use of diamond-film electrodes. Such electrodes are composed of a substrate material, such as silicon or titanium, coated with diamond. Such electrodes are made conductive by doping the diamond film with a conductivity inducing material which promotes p-type semiconductivity to almost metallic levels (e.g., boron).

The unique properties of highly boron-doped diamond (BDD) films include: i) low and stable voltammetric and amperometric background currents, ii) wide working potential window in electrolyte solutions, iii) reversible to quasi-reversible electron transfer kinetics for redox species, iv) morphological and microstructural stability at extreme anodic and cathodic potentials, v) low adsorption of polar molecules, and vi) long-term response stability. Recently it has been reported that BDD films have been coated on several substrates and used to replace earlier electrodes (e.g., gold or platinum) for substrates for electrochemical oxidation of organic wastes. In these uses, the BDD-film electrodes have been reported to be highly robust, capable of withstanding high anodic potentials, and resistant to self-oxidation. An example is the use of a BDD-film electrode for the electrochemical oxidation of phenol. Cyclic voltammetry showed that phenol, one of the most difficult organic molecules to oxidize electrochemically, was oxidized by a BDD-film electrode with no visible oxidation of the electrode itself, even after multiple cycles.

SUMMARY OF THE INVENTION

Figure 1:
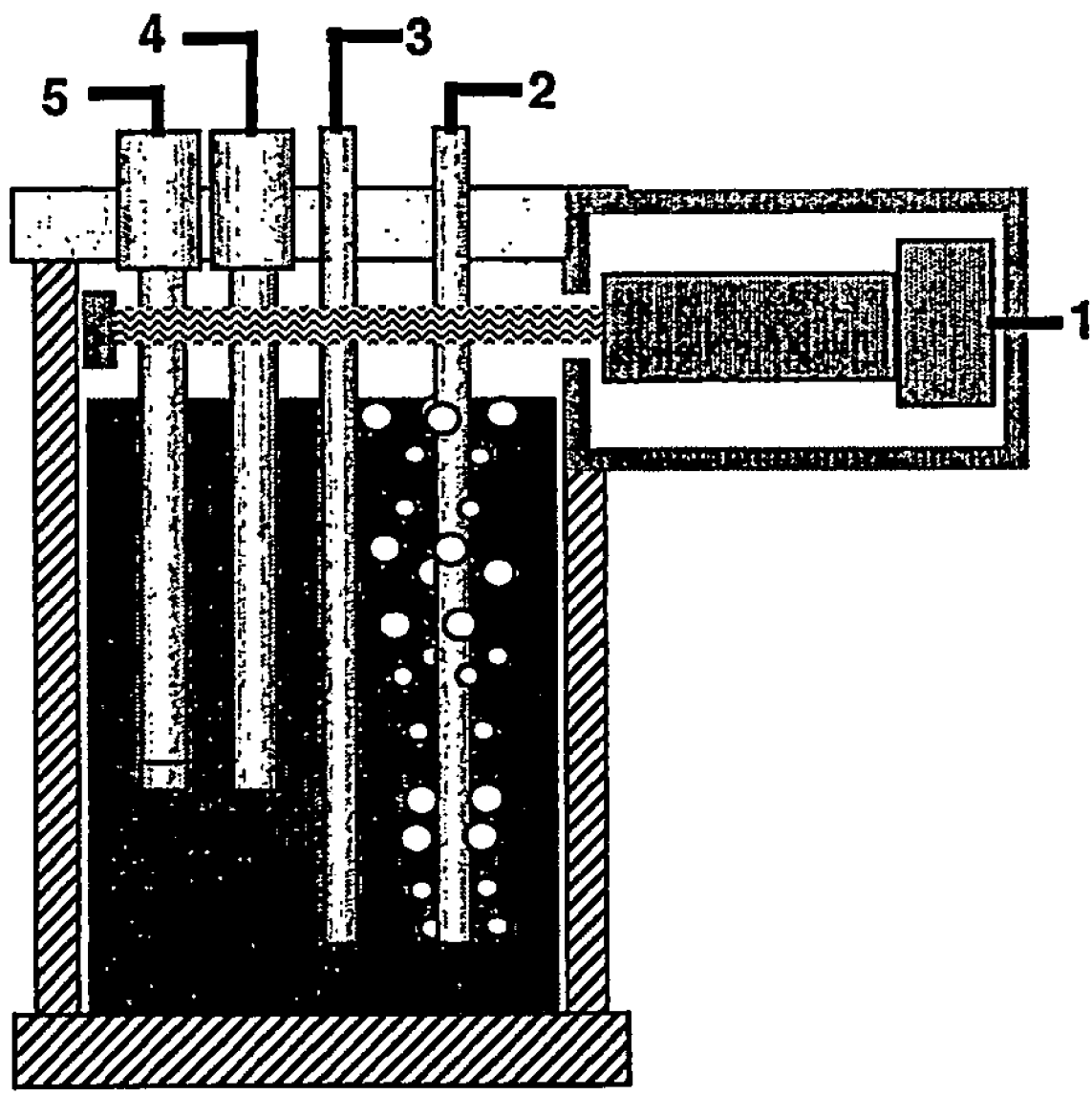
FIG. 1 is a diagrammatic representation of the total organic carbon analyzer apparatus.

The present invention relates to a total organic carbon analyzer apparatus for measuring total organic carbon (TOC) in an aqueous solution. The apparatus comprises an electrochemical cell having a diamond-film electrode, a reference electrode, and a counter electrode. The diamond-film electrode, where the diamond is doped with boron or other suitable atoms which will raise the conductive band of the diamond, is the working electrode and carries out the oxidation of the organic material to produce carbon dioxide. The apparatus further comprises a sensor or sensors for detecting the carbon dioxide produced by the diamond-film electrode. A suitable sensor is one that can detect carbon dioxide at the levels generated by the BDD electrode. Examples of sensors exhibiting this degree of sensitivity include a tunable diode laser spectrometer (TDL) and an ion-selective electrode (ISE).

The instant invention also relates to a method for measuring TOC in an aqueous solution using a total organic carbon analyzer apparatus having a diamond-film electrode. The method provides for immersion of the diamond-film electrode of the electrochemical cell into an aqueous solution to be analyzed for TOC. A positive potential, in the range of about 2-2.5 volts, is applied to the diamond-film electrode to oxidize the organics in the solution and produce carbon dioxide. As previously mentioned, the amount of carbon dioxide produced is detected and measured using a carbon dioxide sensor. The amount of carbon dioxide measured is proportional to the amount of carbon oxidized and is used to calculate the amount of total organics in the solution.

DETAILED DESCRIPTION OF THE INVENTION

Accurate detection and measurement of organics in an aqueous solution has historically required the use of costly methods involving large equipment and the use of hazardous reagents. The use of electrochemical oxidation of carbon with detection of the resultant carbon dioxide gas, promises a versatile, easy to use, and cost-effective alternative for accurately determining TOC levels in a solution. While a variety of electrodes made of different materials are readily available, they are limited in their capacity to effectively oxidize organics.

The present invention relates to the use of an electrochemical cell for carrying out the efficient oxidation of organic carbon to water and carbon dioxide. The working electrode is composed of a substrate material, such as silicon, niobium, or titanium, coated with diamond. The electrode is made conductive by doping the diamond film with boron. The carbon dioxide produced at the electrode surface is detected using an appropriate carbon dioxide sensor.

One aspect of the present invention relates to an apparatus for measuring total organic carbon in an aqueous solution. Such an apparatus includes two principle components contained within a suitable sealed housing to create a closed system so that carbon dioxide generated through the oxidation process can not escape from the system prior to detection. The selection of housing and sealing elements are matters of design choice. The first principle component, an electrochemical cell, is comprised of a working electrode, a reference electrode, and a counter electrode. The working electrode is a diamond-film electrode that is suitable for oxidation of organics in an aqueous sample to produce carbon dioxide. As previously mentioned, the diamond-film is doped with a conductivity inducing material, such as boron.

The second principle component, a carbon dioxide sensor, is used to detect the carbon dioxide produced when the electrochemical cell oxidizes the organics in the sample solution. Carbon dioxide sensors having an appropriate degree of sensitivity for use in connection with the present invention are available in either a gas-phase or aqueous-phase format. An example of a suitable gas phase carbon dioxide sensor is a tunable diode laser (TDL) spectrometer, and an example of a suitable aqueous-phase carbon dioxide sensor is an ion-selective electrode (ISE). Both the TDL and ISE sensors are known in the art. The device of the present invention may include one or more carbon dioxide sensors. In preferred embodiments, where only one sensor is provided, that one sensor is a gas-phase carbon dioxide sensor. The gas phase sensor is used to detect carbon dioxide gas bubbled from the aqueous solution containing the organic being oxidized. To quantitate levels of organic in the aqueous solution using a single gas phase sensor, it is necessary to convert substantially all of the organic material in the sample to carbon dioxide and water, and to allow sufficient time for dissolved carbon dioxide to bubble from solution. Alternatively, a combination of a gas-phase sensor and an aqueous-phase sensor may be used to quantitate organics in solution. When a combination of sensors is employed, it is not necessary to allow all dissolved carbon dioxide to bubble into the head space of the closed system (see FIG. 1, for example) wherein it can be measured using a gas-phase sensor. Rather, a liquid-phase sensor (e.g., an ISE) is useful for measuring levels of dissolved carbon dioxide in the aqueous-phase, and the gas-phase sensor (e.g., a TDL) measures the gas phase carbon dioxide in the head space. Assuming that the conversion from organic to carbon dioxide and water is substantially complete, the sum of the gas-phase and aqueous-phase carbon dioxide levels can be used to calculate concentrations of the organic originally present in the aqueous sample.

Such an apparatus, comprising an electrochemical cell having a working electrode made of boron-doped diamond and a TDL carbon dioxide spectrometer or ISE, may be manufactured to be compact and of relatively small size as compared to existing devices intended for similar application. Given the relatively compact formats achievable based on present disclosure, the device of the present invention is particularly well-suited for portable field use.

Another aspect of the present invention relates to a method for measuring total organic carbon in an aqueous solution. First, the diamond-film electrode is brought into contact with a volume of a sample to be tested for its level of total organics. The sample is an aqueous solution, such as water from a municipality, or a solution containing a dissolved specimen.

The electrode may be immersed into the sample solution or a flow-cell may be used, where the sample is circulated through the cell and in contact with the diamond-film electrode. To achieve optimal oxidation of organics in the sample, a positive potential in the range of about 2-2.5 volts is applied to the diamond-film electrode. In preferred embodiments, the positive potential is provided by an external battery. This current will cause oxidation of organics to occur, producing carbon dioxide at the surface of the diamond-film electrode. The carbon dioxide may bubble into a collector chamber (e.g., the headspace above the aqueous solution in FIG. 1) in communication with the carbon dioxide sensor where it is measured spectroscopically and recorded in absorption units (AU). The carbon dioxide may also be dissolved in the aqueous solution where it can be measured by an ISE selective for carbon dioxide and recorded as an electric potential in volts (V).

The TDL may be a small laser diode that produces a very narrow and specific wavelength of light tuned to the harmonic frequency of the carbon dioxide gas molecule in the near infrared band. To specifically measure carbon dioxide with a TDL, the TDL is preferably tuned to the harmonic frequency of carbon dioxide molecules in the near-infrared band. After being adjusted to the carbon dioxide frequency, the tunable laser diode may be tuned to different wavelengths on either side of the carbon dioxide wavelength. The light energy being absorbed by the carbon dioxide is then compared to calibrated values at the surrounding frequencies to obtain a precise quantitative measurement of the amount of carbon dioxide produced. The amount of carbon dioxide measured will be directly proportional to the amount of organics that were present in the aqueous sample. Using aqueous samples containing known quantities of dissolved organics, a standard curve may be generated to allow for the determination of precise concentration of organics within the test solution.

An Ion Selective Electrode (ISE) is a membrane electrode that responds selectively to certain ions in the presence of other ions. The ISE is particularly useful in the present invention for the detection of dissolved carbon dioxide generated by the breakdown of organic compounds at the working electrode. Such dissolved carbon dioxide may be measured by the ISE prior to its buildup in the headspace above the sample solution, where the TDL is useful. To specifically measure carbon dioxide with an ISE, the membrane of the ISE is selected such that carbon dioxide molecules selectively cross the membrane—such ISEs selective for carbon dioxide are well known in the art. The ISE is brought into contact with the sample solution and the potential at the ISE is then compared to that of the reference electrode. The magnitude of the potential at the ISE vs. the reference electrode is directly proportional to the concentration of carbon dioxide dissolved in the aqueous sample. The amount of carbon dioxide measured will be directly proportional to the amount of organics that were present in the aqueous sample. Using aqueous samples containing known quantities of dissolved organics, a standard curve may be generated to allow for the determination of precise concentration of organics within the test solution.

FIG. 1 is a diagrammatic representation of an embodiment of the present invention. The apparatus comprises an electrochemical cell having a diamond-film electrode 2, a reference electrode 4, and a counter electrode 3. The diamond-film electrode 2 is the working electrode and carries out the oxidation of the organic material to produce carbon dioxide. The apparatus further comprises a carbon dioxide sensor for detecting the carbon dioxide produced by the diamond-film electrode. Examples of suitable sensors include a tunable diode laser spectrometer (TDL) 1 and an ion-selective electrode (ISE) 5.

The invention claimed is:

1. An apparatus for measuring total organic carbon in an aqueous solution, consisting essentially of:
    a) an electrochemical cell comprising: i) a diamond-film electrode; ii) a reference electrode; iii) an aqueous solution; and iv) a counter electrode; and
    b) one or more carbon dioxide sensors, including at least one gas-phase sensor.

2. The apparatus of claim 1 wherein the diamond-film electrode is doped with a conductivity inducing material.

3. The apparatus of claim 2 wherein the conductivity inducing material is boron.

4. The apparatus of claim 1 wherein the gas-phase sensor is a tunable diode laser spectrometer.

5. The apparatus of claim 1 further comprising an aqueous-phase carbon dioxide sensor.

6. The apparatus of claim 5 wherein the aqueous-phase sensor is an ion-selective electrode.

7. The method of claim 6 wherein the gas-phase sensor is a tunable diode laser spectrometer.

8. The method of claim 6 wherein the diamond-film electrode is doped with a conductivity inducing material.

9. The method of claim 8 wherein the conductivity inducing material is boron.

10. The method of claim 6 wherein the positive potential is in the range of about 2-2.5 volts.

11. A method for measuring total organic carbon in an aqueous solution, the method comprising:
    a) providing an electrochemical cell comprising of: i) a diamond-film electrode; ii) a reference electrode; and iii) a counter electrode;
    b) immersing the electrochemical cell of step a) into the aqueous solution;
    c) applying a positive potential to the diamond-film electrode, the positive potential being sufficient to oxidize organics in the solution, thereby producing water and carbon dioxide;
    d) measuring the amount of carbon dioxide produced in step c) using one or more carbon dioxide sensors, including at least one gas-phase sensor measuring carbon dioxide above the aqueous solution; and
    e) determining the amount of total organic carbon in the solution, the amount of total organic carbon being proportional to the amount of carbon dioxide measured in step d).

12. A method for measuring total organic carbon in an aqueous solution, the method comprising:
    a) providing an electrochemical cell comprising of: i) a diamond-film electrode; ii) a reference electrode; and iii) a counter electrode;
    b) immersing the electrochemical cell of step a) into the aqueous solution;
    c) applying a positive potential to the diamond-film electrode, the positive potential being sufficient to oxidize organics in the solution, thereby producing water and carbon dioxide;
    d) measuring the amount of carbon dioxide produced in step c) using two or more carbon dioxide sensors, including at least one gas-phase sensor measuring carbon dioxide above the aqueous solution, and at least one aqueous-phase sensor; and
    e) determining the amount of total organic carbon in the solution, the amount of total organic carbon being proportional to the amount of carbon dioxide measured in step d).

13. The method of claim 12 wherein the aqueous-phase sensor is an ion-selective electrode.

* * * * *